United States Patent [19]
Wille et al.

[11] Patent Number: 5,618,557
[45] Date of Patent: Apr. 8, 1997

[54] PROPHYLACTIC TREATMENT OF ALLERGIC CONTACT DERMATITIS

[75] Inventors: John J. Wille, Trenton; Agis Kydonieus, Kendall Park; Frank S. Castellana, Princeton, all of N.J.

[73] Assignee: E.R. Squibb & Sons, Inc., Princeton, N.J.

[21] Appl. No.: 343,157

[22] Filed: Nov. 22, 1994

[51] Int. Cl.$^6$ .................................................. A61F 13/00
[52] U.S. Cl. ........................... 424/449; 424/447; 514/885; 514/922
[58] Field of Search ................... 424/449, 447; 514/885, 922

[56] References Cited

U.S. PATENT DOCUMENTS

| | | | |
|---|---|---|---|
| 3,968,245 | 7/1976 | Higuchi | 424/400 |
| 4,888,354 | 12/1989 | Chang et al. | 514/424 |
| 5,120,545 | 6/1992 | Ledger | 424/449 |
| 5,164,509 | 11/1992 | Atwal | 548/126 |

FOREIGN PATENT DOCUMENTS 9009792  9/1990  WIPO.

*Primary Examiner*—D. Gabrielle Phelan
*Attorney, Agent, or Firm*—Theodore R. Furman, Jr.; John M. Kilcoyne

[57] ABSTRACT

Methods and devices for preventing an adverse reaction of the skin to the presence of a skin-sensitizing agent by administering an effective amount of a potassium-sparing diuretic.

16 Claims, No Drawings

PROPHYLACTIC TREATMENT OF ALLERGIC CONTACT DERMATITIS

FIELD OF THE INVENTION

The present invention relates to methods and compositions for preventing adverse reactions of the skin in general to skin-sensitizing agents and especially adverse reactions occasioned by the cutaneous administration of a therapeutic agent for transdermal applications.

BACKGROUND OF THE INVENTION

Allergic reactions of the skin to various agents known as allergic contact dermatitis (ACD), is an immune response that occurs in the skin. The response is the result of the penetration of the skin by a foreign substance (e.g. hapten or antigen) that provokes a skin sensitization reaction. ACD is a two phase process involving an initial induction phase followed by an elicitation phase.

The induction phase occurs immediately after first time exposure of the skin to the hapten or antigen and is characterized by the formation of immune memory cells that can subsequently recognize the specific hapten or antigen which previously entered the skin for the first time.

The elicitation phase occurs when the skin is subsequently re-exposed to the original hapten or antigen. In the elicitation phase, the skin provides an overt reaction to the presence of the hapten or antigen in the form of a skin inflammatory response.

ACD generally results in a life-time persistent memory for the specific hapten or antigen. Thus, when the skin is exposed to the hapten or antigen at a subsequent time, there is typically an immediate and often severe skin inflammatory response.

Agents that cause allergic contact dermatitis are varied and numerous and include, for example, metals (e.g. nickel, chromium, cobalt and the like) fragrances, chemicals, cosmetics, textiles, pesticides, plastics, pollen and the like (see, for example, R. J. G. Rycroft et al. "Textbook of Contact Dermatitis"). Therapeutic agents such as drugs may also cause allergic contact dermatitis particularly when administered transdermally.

The transdermal route of parenteral delivery of drugs provides many advantages over alternate routes of administration. Transdermal delivery systems (TDS) for delivery of drugs or other beneficial agents are well-known (see, for example, U.S. Pat. Nos. 3,598,122, 3,598,123, 4,286,592, 4,314,557, 4,379,454, 4,599,222 and 4,573,995, which are each incorporated herein by reference). A TDS is generally composed of the following components: (a) "basic components", including backing, matrix reservoir, and an optional separate adhesive layer; (b) the drug or other therapeutic agent; (c) "additives", including solubilizers, plasticizers and permeation enhancers; and (d) "impurities" such as residual amounts of monomers, initiators, cross-linkers, etc., from the polymerization process during fabrication of the basic components.

However, TDS provide conditions highly conducive for the induction of skin allergic reactions, and the following skin reactions may be expected to occur:

1. Irritant reactions to the drug, an additive, an impurity, or a combination thereof;
2. Allergic reactions, especially to the low molecular weight components (drug, additive, impurity, adhesive);
3. Prolonged skin occlusion causes blocking of sweat ducts favoring local sweat retention syndrome.

Allergic contact dermatitis presents a significant problem in the transdermal administration of therapeutic agents. It is well known that many drugs, including some currently marketed in the United States (e.g. clonidine) sensitize the skin when used in a transdermal delivery system. Skin inflammation may be produced not only by the transdermally delivered drug, but also by a non-sensitizing drug combined with skin sensitizing permeation enhancers, or a combination of a sensitizing drug and a sensitizing permeation enhancer. Penetration of these sensitizing agents into the skin and the resulting skin irritation may persist well beyond the time that the transdermal patch is removed from the skin. The local inflammation may be a source of discomfort and a clinical complication in a patient suffering from such a reaction.

Efforts have been made to address the problem of allergic contact dermatitis by prophylactically treating the skin to prevent the onset of the induction phase of ACD and/or to therapeutically prevent or reduce the adverse effects of the elicitation phase of ACD. For example, U.S. Pat. No. 5,202,130 discloses that lanthanide ions and organic calcium channel blockers individually can be used for the treatment of contact allergic dermatitis.

Wolfgang Diezel et al., *J. Invest. Derm.*, Vol. 93, No. 3, pp. 322–326 (September 1989) discloses the sensitization of mice with 1-chloro-2, 4-dinitrobenzene and subsequent treatment with lanthanum citrate and diltiazem hydrochloride to prevent the onset of the induction phase of the sensitizing agent. Philip W. Ledger, et al., U.S. Pat. No. 5,120,545 disclose the prevention of skin sensitization by the administration of an antigen processing-inhibiting agent such as ammonium chloride. A method of preventing contact sensitization using steroids (e.g. corticosteroid and glucocorticoid carboxylic acid esters) is disclosed, for example, in Alfred Amkraut, U.S. Pat. No. 5,118,509 and Peter M. Ross, et al., U.S. Pat. No. 4,897,260.

Methods of treating ACD through the blocking of the elicitation phase is disclosed, for example, in John McFadden, et al., *J. Invest. Derm.*, Vol. 99, No. 6, pp. 784–786 (December 1992). Tuberculin-induced delayed-type hypersensitivity reaction in human skin was inhibited by topical applications of verapil hydrochloride prior to or concurrent with challenge with tuberculin.

Also, Richard L. Gallo, et al., *Arch. Dermatol.*, Vol. 125, pp. 502–506 (April 1989) and WO 90/09792 published Sep. 7, 1990 disclose the administration of the diuretic amiloride and its analogs as a topical agent for the treatment of ACD, particularly mice sensitized with 2,4,6-trinitrobenzene.

Despite these efforts and the knowledge gained regarding the cause of ACD, there remains a need to develop compositions which effectively prevent the onset of ACD in a person who has been sensitized to an agent, as for example a transdermally administered agent such as a drug.

Applicants have discovered that a particular class of compounds having diuretic properties, referred to herein as potassium-sparring diuretics, achieve significant prevention against sensitization of a patient's skin. As a result, an adverse reaction of the skin to a skin-sensitizing agent such as therapeutic agents administered transdermally is prevented or minimized allowing for the administration of agents that could not previously be administered and/or have longer dosage regimens. The present invention therefore provides prevention of an adverse reaction to the skin, as well as a transdermal therapy which reduces discomfort to the patient.

SUMMARY OF THE INVENTION

The present invention is generally directed to methods of preventing allergic contact dermatitis (ACD) and compounds and systems, especially transdermal systems, used in said methods. In one aspect of the invention a method is provided for preventing an adverse reaction of the skin caused by the presence of skin-sensitizing agents such as metals, fragrances, cosmetics, textiles, pollen, pesticides, plastics and the like. The present invention is also applicable to ACD induced by the transdermal administration of an agent, as for example, a therapeutic agent such as a drug. The method of the present invention comprises administering to the skin of a warm-blooded animal an effective amount of at least one potassium-sparing diuretic.

The agents employed in the present invention for preventing skin irritation or inflammation from ACD caused by any skin-sensitizing agent can be prepared in the form of a composition containing one or more additives including skin permeation enhancers, excipients and the like.

These adverse skin reaction preventing agents may be administered topically in the form of lotions, creams, sprays and the like, by non-cutaneous routes as well as through the use of transdermal patches. In transdermal applications, the agents may be administered from a single reservoir also containing the therapeutic agent or preferably from a separate reservoir of a transdermal patch.

DETAILED DESCRIPTION OF THE INVENTION

The present invention is generally directed to methods and systems for preventing the onset of skin irritation or inflammation caused by allergic contact dermatitis. In one aspect of the invention the skin is treated with a prophylactically-effective amount of at least one potassium-sparing diuretic. The employment of a composition containing such adverse skin reaction preventing agents provides inhibition of the immune response and specific immune tolerance to the provoking antigen.

More specifically, a single administration to the skin of a potassium-sparing diuretic renders a warm-blooded animal specifically unresponsive to an antigen, a state known as immunological tolerance. Three immunosuppressive agents known to induce immune tolerance are UVB radiation, the cytokine TNF-α, and cis-urocanic acid. A number of mechanisms are thought to be responsible for the induction and maintenance of this tolerant state. Regardless of the mechanism, it is well-known that tolerance to an antigen which stimulates a sensitization response can be induced first by presenting the antigen in a tolerogenic form or via a tolerogenic route. The present invention encompasses a method wherein the immune response of an antigen is suppressed and a state of prolonged immunological tolerance is achieved.

Potassium-sparing diuretics of the type employed in the present invention for achieving the state of prolonged immunological tolerance such as amiloride, inhibit sodium ion and hydrogen ion transport processes at the cell membrane. They alter the signal transduction processes requisite to the acquisition of immune cell memory, a vital aspect of the induction phase of the sensitization response. A mechanism of action thought to be involved is the selective inhibition of the sodium/hydrogen ion channel ATPase enzyme. Inhibition of this enzyme results in an elevation of intracellular pH, and ultimately to a block in intracellular production of second messenger and/or gene transcription initiated by signal transduction mechanisms.

Examples of potassium-sparing diuretics for use in the present invention include amiloride and triamterene, and analogs thereof. Amiloride is the preferred potassium-sparing diuretic. Amiloride and its analogs are disclosed in WO/09792 published Sep. 7, 1990 and is incorporated herein by reference.

The above methods are useful for preventing skin irritation or inflammation produced by a variety of skin-sensitizing agents such as, for example, a drug selected from, but not limited to, the following group: (a) an angiotensin converting enzyme inhibitor; (b) a beta adrenergic receptor blocker; (c) an antihypertensive drug other than an angiotensin converting enzyme inhibitor or a beta adrenergic receptor blocker; (d) an antihistamine; (e) an anti-asthmatic; (f) a non-steroidal antiinflammatory drug; (g) a central nervous system active drug; (h) a weight control drug; (i) an anticoagulant; (j) a potassium control drug; (k) an immunomodulatory drug; (l) a decongestant; and (m) proteins and peptides such as insulin and thyrotropinreleasing hormone.

More specifically, the therapeutic agents for administration in accordance with the present invention include all of the major therapeutic areas, including, but not limited to: antiinfectives, such as antibiotics and antivirals; analgesics and analgesic combinations; anorexics; antiarthritics; anti-asthmatics (such as albuterol, metaproterenol, ketotifen and terbutaline); anticoagulants (such as urokinase); anticonvulsants; antidepressants; anti-diabetics; antidiarrheals; antihistamines (such as chlorpheniramine and diphenhydramine); anti-inflammatory agents (such as ketoprofen, prostaglandins, flurbiprofen, diclofenac, indomethacin, piroxicam and ibuprofen); antimigrane agents; anti-motion sickness preparations; antinauseants; antineoplastics; antiparkinsonism drugs; antipruritics; antipsychotics; antipyretics; antispasmodics, including gastrointestinal and urinary; anticholinergics; sympathomimetics; xanthine derivatives; cardiovascular agents, including angiotensin converting enzyme inhibitors (such as captropril and fosinopril); beta blockers (such as nadolol, timolol, propranolol and alprenolol); anti-arrythmics; antihypertensives (such as clonidine); vasodilators, including general, coronary, peripheral and cerebral; central nervous system acting agents (such as fluphenazine, trifluoperazine, haloperidol, Xanax®, Librium®, Valium®); cough and cold preparations; decongestants; diagnostics; hormones; hypnotics; muscle relaxants; parasympatholytics; parasympathomimetics; psychostimulants; sedatives; weight control and appetite suppressive drugs (such as mazindol) and tranquilizers.

The present invention further provides an article useful for preventing the skin irritating or inflammatory effect of a component of a transdermal drug delivery system, where the component is either a drug, a skin permeation enhancer or a combination of the two and the like, the article comprising:

(a) a transdermal delivery system comprising a therapeutic agent (e.g. a drug) of interest; and (b) an effective amount of at least one potassium-sparing diuretic.

The adverse skin reaction preventing agents can also be administered in a transdermal or a controlled-release device. Examples of transdermal devices and delivery systems which may be used are disclosed in Bodde, H. E. et al., Crit. Rev. Ther. Drug Carrier Syst. 6: 87–115 (1989); and in U.S. Pat. Nos. 3,598,122, 3,598,123, 4,286,592, 4,314,557, 4,379,454, 4,559,222, 4,573,995, which references are hereby incorporated by reference.

The delivery system may include a first transdermal device comprising a matrix for placing the potassium-sparing diuretic in transmitting relationship to the skin. A second transdermal device may be used to place the therapeutic agent in transmitting relationship to the skin after the potassium-sparing diuretic has been transdermally administered to the skin. The first and second transdermal devices may be incorporated into a single transdermal patch.

The potassium-sparing diuretics are administered by themselves or, in transdermal systems in combination with a therapeutic agent of interest. These agents may be administered topically or non-cutaneously such as by intradermally, intravenously, intramuscularly, orally or intra-peritoneally. The agents of the present invention can be incorporated into a pharmaceutically acceptable composition for topical application to the skin in the form of lotions, creams gels and the like. Useful carriers for the preparations of such compositions include water, ethanol, gels and the like.

The precise formulation of the transdermally administered therapeutic agent (e.g. a drug) and the potassium-sparing diuretics of the present invention can be designed to deliver the drug and the diuretics at the desired fluxes and can be in numerous forms, including, without limitation, ointments, gels and creams. Aqueous formulations, in particular gels, typically comprise water and from about 1 to 2.5% (w/w) of a gelling agent such as hydroxyethylcellulose or hydroxypropylmethylcellulose (HPMC). Typical non-aqueous gels comprise silicone fluid or mineral oil. The mineral oil may also have 1 to 2% (w/w) of a gelling agent such as colloidal silicon dioxide. The suitability of a particular gel composition depends on the compatibility of its constituents with the drug (with or without a permeation enhancer) and the adverse skin reaction preventing agents.

In another embodiment, the potassium-sparing diuretics are delivered to the skin prior to the administration of the therapeutic drug or drugs. Such prior administration can be via transdermal application using a device as described above, via topical application, intracutaneous injection, and the like.

In yet another embodiment, the potassium-sparing diuretics are delivered by another non-cutaneous route and method of delivery, either concurrently with, or prior to, the transdermal administration of the therapeutic drug.

In all of the above embodiments, the dosage of the potassium-sparing diuretics administered will be dependent upon the agent, the age, health, and weight of the recipient, kind of concurrent treatment, if any, and frequency of treatment.

The methods and compositions within the scope of this invention include all compositions and methods wherein the potassium-sparing diuretics are contained in an amount effective to achieve their intended purpose. While individual needs vary, determination of optimal ranges of effective amounts of each component is within the skill of the art.

For transdermal administration, typical effective dosages of the potassium-sparing diuretics to prevent ACD by a sensitizing drug will depend on their permeation through human skin, and is a function of the physical properties of the permeant, including the partition coefficient of the permeant between solvent and skin, molecular weight and melting point. In general, the maximum flux that can be obtained from any permeant occurs from saturated solutions. Equations have been derived that predict accurately the maximum flux given the partition coefficient, molecular weight and melting point of the permeant as described in, for example, "TREATISE ON CONTROLLED DRUG DELIVERY", A. Kydonieus, ed., Marcel Dekker, Inc., New York, 1991, in particular, p. 370, equations 3a and 4a and p. 34, FIG. 2, incorporated herein by reference. For example, for the transdermal delivery of the potassium-sparing diuretics, including the preferred compound amiloride the expected maximum flux that can be delivered locally to skin is in the range of from about 1 to 50 $ug/cm^2/hr$. This value is dependent, for example on varying skin age, skin type and skin condition. The preferred range for the maximum flux is from about 5 to 25 $ug/cm^2/hr$. Accordingly, as will be understood by those skilled in the art, the delivery of a particular potassium-sparing diuretic, is controlled by the percent saturation of that agent in the chosen vehicle.

The amount of the potassium-sparing diuretic which can be delivered to prevent ACD will vary from patient to patient. For example, the amount of amiloride delivered from a gel formulation (2.5% HPMC in 75% ethanol and 5% dimethyl sulfoxide (DMSO)) is from about 0.5 to 5.0% by weight.

EXAMPLE 1

A 1.0% (w/v) solution of amiloride was prepared in gel formulation (2.5% HPMC in 75% ethanol and 5% DMSO). The same gel formulation served as a negative control. For sensitization, a 1% (w/v) solution of dinitrochlorobenzene (DNCB) was prepared in acetone.

Twenty-four (24) Balb/c mice had their abdominal skin shaved. The mice were divided into three equal groups. The first group acted as a negative control and received on day 0 an application of 0.2 mL of hydroxypropylmethylcellulose (HPMC) on their exposed abdominal skin. The second group acted as a positive control by receiving on day 0, 0.2 mL of HPMC gel on exposed abdominal skin. The third group of mice was treated with 0.2 mL of HPMC gel containing amiloride on day 0.

Twenty-four (24) hours later, the mice in Groups II and III received ten (10) microliters of 1% DNCB solution over the skin area pretreated with gel, while the mice in Group I received ten (10) microliters of acetone. All three groups were challenged on the right ear with twenty (20) microliters of 1% DNCB in acetone five (5) days after sensitization.

Adverse reaction to the challenge with DNCB was determined by measuring the thickness of the mice ears before and after challenge to determine the amount of swelling, and then comparing the degree of swelling for mice treated in accordance with the invention (Group III) with Groups I and Groups II. The results are shown in Table 1.

TABLE 1

| TREATMENT | EAR THICKNESS (MM × $10^{-3}$) | EAR SWELLING (MM × $10^{-3}$) | % SUPPRESSION |
|---|---|---|---|
| GROUP I NONE (HPMC GEL) | | | |
| 24 HOURS | 249 ± 9 | — | — |
| 48 HOURS | 247 ± 8 | — | — |
| GROUP II | | | |

TABLE 1-continued

| TREATMENT | EAR THICKNESS (MM × 10⁻³) | EAR SWELLING (MM × 10⁻³) | % SUPPRESSION |
|---|---|---|---|
| DNCB ONLY (100 µg) | | | |
| 24 HOURS | 334 ± 35 | 86 | — |
| 48 HOURS | 336 ± 23 | 89 | — |
| GROUP III AMILORIDE 2 MG (1%) (HPMC GEL) (PRETREAT) + DNCB (100 µg) | | | |
| 24 HOURS | 278 ± 31 | 29 | 66 |
| 48 HOURS | 301 ± 43 | 53 | 40 |

As shown in Table 1, the Group II mice exhibited significant ear swelling when sensitized to DNCB. The potassium-sparing diuretic constituting an adverse skin reaction preventing agent of the present invention when administered prophylactically limits inflammation induced by DNCB.

EXAMPLE 2

Induction of Immune Tolerance by Amiloride

The procedures used for Example 1 were repeated except that forty-eight (48) animals had their abdominal skin shaved. The mice were then divided into six (6) equal groups. The first three groups, I, II, and III, were treated exactly like the correspondingly numbered groups of Example 1. The last three groups IV, V and VI were pre-treated with gel on day 0 like Groups I, II and III, and Groups V and VI were sensitized with ten (10) microliters of 1% DNCB over the skin area pre-treated with gel. However, when Groups I, II and III were challenged five (5) days after sensitization, Groups IV, V, and VI received twenty (20) microliters of acetone on their right ears.

Adverse reaction to challenge with 1% DNCB in acetone for Groups I, II and III was measured by the same procedures used in Example 1. The results of the challenge on ear swelling for Groups I, II and III are shown in Table 2. The In order to demonstrate that the potassium-sparing diuretics (e.g. amiloride) produce a state of immune non-responsiveness, i.e., immune tolerance, the backs of animals in Groups IV, V and VI were shaved eighteen days after receiving on day 0 either control or amiloride containing gels. Animals in Group IV received ten (10) microliters of acetone on their exposed back skin, and animals in Groups V and VI were re-sensitized at the second skin site by applying 1% DNCB in acetone on their exposed back skin. All three groups were challenged on the left ear with twenty (20) micro liters of 1% DNCB in acetone five (5) days after sensitization on the back. The results of the challenge on ear swelling for Groups IV, V and VI are shown in Table 2.

As shown in Table 2, Group V mice exhibited significant ear swelling similar to Group II of this example. The potassium-sparing diuretic constituting an adverse skin reaction preventing agent of the present invention when administered prophylactically to the primary skin site (abdomen) on day 0, and when those same animals were re-sensitized on a secondary skin site (back) limits skin inflammation twenty-four (24) hours after challenge. This example provides clear evidence that a single topical application of the potassium-sparing diuretic (e.g. amiloride) produces immune tolerance to the sensitizing agent.

TABLE 2

| TREATMENT | EAR THICKNESS (MM × 10⁻³) | EAR SWELLING (MM × 10⁻³) | % SUPPRESSION |
|---|---|---|---|
| GROUP I NONE (HPMC Gel only) 24 hours | 249 ± 9 | — | — |
| GROUP IV Day 18–19: 24 hours | 238 ± 13 | — | — |
| GROUP II DNCB ONLY (100 µg) 24 hours | 343 ± 38 | 94 | — |
| GROUP V Day 18–19: 24 hours | 348 ± 37 | 110 | — |
| GROUP III Amiloride 2 mg (1%) + DNCB (100 µg) 24 hours | 295 ± 13 | 46 | 50.6 |
| GROUP VI Day 18–19: 24 hours | 307 ± 40 | 70 | 36.6 |

Group II mice exhibited significant ear swelling when sensitized to DNCB. The potassium-sparing diuretic (1% amiloride), when administered prophylactically limited skin inflammation.

What is claimed is:

1. A method of preventing a sensitization reaction of the skin of a warm-blooded animal to the presence of a skin-sensitizing material comprising administering to said warm-blooded animal before the onset of a sensitization reaction an amount of at least one potassium-sparing diuretic sufficient to prevent said skin sensitization reaction, said amount being insufficient to impart a diuretic effect to said warm-blooded animal.

2. The method of claim 1 wherein the skin-sensitizing material is a drug.

3. The method of claim 1 wherein the skin-sensitizing material is administered transdermally.

4. The method of claim 1 wherein the potassium-sparing diuretic is administered transdermally.

5. The method of claim 3 wherein the potassium-sparing diuretic is administered transdermally.

6. The method of claim 1 wherein the potassium-sparing diuretic is selected from the group consisting of amiloride and triamterene.

7. The method of claim 6 wherein the potassium-sparing diuretic is amiloride.

8. The method of claim 5 comprising administering the potassium-sparing diuretic and the skin-sensitizing material by a transdermal patch.

9. The method of claim 4 wherein the maximum flux of the potassium-sparing diuretic is from about 1 to 50 µg/cm$^2$/hr.

10. The method of claim 9 wherein the maximum flux of the potassium-sparing diuretic is from about 5 to 25 µg/cm$^2$/hr.

11. A transdermal delivery system for preventing a sensitization reaction of the skin of a warm-blooded animal to the presence of a skin-sensitizing material by the administration to said warm-blooded animal of an amount of at least one potassium-sparing diuretic sufficient to prevent said skin-sensitization reaction, said amount being insufficient to impart a diuretic effect on said warm-blooded animal, said transdermal delivery system comprising:

a) a first transdermal device comprising a matrix for placing the potassium-sparing diuretic in transmitting relationship to the skin; and b) a second transdermal device comprising a matrix for placing a therapeutic material in transmitting relationship to the skin after the potassium-sparing diuretic has been transdermally administered to the skin from the first transdermal device.

12. The transdermal delivery system of claim 11 wherein the first and second transdermal devices are contained within a single transdermal patch.

13. A method of transdermally administering to a warm-blooded animal a therapeutic material without thereby eliciting a sensitization reaction from the skin comprising transdermally administering before, during or after the administration of the therapeutic material an amount of at least one potassium-sparing diuretic sufficient to prevent said sensitization reaction, said amount being insufficient to impart a diuretic effect to said warm-blooded animal.

14. The method of claim 13 wherein the potassium-sparing diuretic is selected from the group consisting of amiloride and triamterene.

15. A method of imparting an immunological tolerance to the skin of a warm-blooded animal to the presence of a skin-sensitizing material comprising administering to said warm-blooded animal before the onset of said skin-sensitization reaction, an amount of at least one potassium-sparing diuretic sufficient to impart said immunological tolerance, said amount being insufficient to impart a diuretic effect to said warm-blooded animal.

16. The method of claim 15 wherein said potassium-sparing diuretic is selected from amiloride and triamterene.

* * * * *